United States Patent [19]

Sobolev

[11] Patent Number: 4,861,744
[45] Date of Patent: Aug. 29, 1989

[54] PROCESS FOR PREPARING A FLUORINATION CATALYST AND THE CATALYST PREPARED BY THE PROCESS

[75] Inventor: Igor Sobolev, Orinda, Calif.

[73] Assignee: LaRoche Chemicals, Inc., Baton Rouge, La.

[21] Appl. No.: 248,841

[22] Filed: Sep. 26, 1988

Related U.S. Application Data

[62] Division of Ser. No. 62,655, Jun. 16, 1987, Pat. No. 4,792,643.

[51] Int. Cl.$^4$ ............... B01J 27/12; B01J 27/132; B01J 27/135
[52] U.S. Cl. ..................... 502/227; 502/228
[58] Field of Search ............... 502/227, 228

[56] References Cited

U.S. PATENT DOCUMENTS 3,787,331  1/1974  Groppelli et al. ............ 502/228

Primary Examiner—W. J. Shine
Attorney, Agent, or Firm—Andrew E. Barlay

[57] ABSTRACT

A novel catalyst is prepared by codepositing hexavalent chromium oxide and a transition metal compound, preferably titanium trichloride, on alumina, followed by fluorinating the resulting combination. The catalyst is useful in the fluorination of a haloethylene of the formula $CX_2=CHX$ (where the X's are chlorine or bromine or a combination of the two) in the vapor phase to form 1,1,1,2-tetrafluoroethane.

11 Claims, No Drawings

PROCESS FOR PREPARING A FLUORINATION CATALYST AND THE CATALYST PREPARED BY THE PROCESS

This application is a divisional application of Ser. No. 07/062,655, filed on June 16, 1987 now U.S. Pat. No. 4,792,643.

This invention relates to the fluorination of a trihaloethylene, where the halogens are chlorine or bromine, to 1,1,1,2-tetrafluoroethane. In particular, this invention relates to vapor phase reactions for this fluorination using a chromium-based catalyst.

BACKGROUND OF THE INVENTION

The fluorocarbons chlorotrifluoromethane and dichlorodifluoromethane have received extensive use in refrigerants, foam blowing agents and other applications. They are members of a group of chlorofluorocarbons referred to as FC or CFC 11 and 12, respectively. Because of their stability and long atmospheric lifetime, there has been concern about possible effects of these fully halogenated fluorocarbons on stratospheric ozone. This concern has spurred the search for replacements that are free of chlorine or, due to the presence of a reactive hydrogen, will have a much shorter atmospheric lifetime. A notable candidate, particularly for the replacement of FC 12, is 1,1,1,2,-tetrafluoroethane, also known as FC 134a.

Unfortunately, synthesis of this compound is difficult, and isomers and a variety of byproducts generally dominate reaction product mixtures. The following is a review of the pertinent known reactions.

The use of trichloroethylene as a starting material is described in two patents to Ruh et al. (Dow Chemical), Nos. 2,745,886 (May 15, 1956) and 2,885,427 (May 5, 1959). The catalyst is an oxygenated chromium (III) fluoride obtained by burning $CrF_3.3H_2O$ in oxygen at 600° C. The highest yield reported for 1,1,1,2-tetrafluoroethane, however, was only 3% (mole basis).

The product has also been prepared by the fluorination of 1,1,1-trifluoro-2-chloroethane in various processes. One is described by Bell (ICI), U.S. Pat. No. 4,129,603 (Dec. 12, 1978), in which chromium oxide or basic chromium fluoride is used as a catalyst. A metal permanganate is then used to destroy 1,1-difluoro-2-chloroethylene produced as an impurity. A similar disclosure appears in Potter (ICI), U.S. Pat. No. 4,158,675 (June 19, 1979), except that additional hydrogen fluoride at a controlled temperature is used for conversion in place of the metal permanganate. Daikin Kogyo KK in British Pat. No. 2,030,981 (Mar. 2, 1983) describe the use of a chromium (III) compound as a catalyst with oxygen fed to the reaction system as a means of preventing loss of catalytic activity. Gumprecht (DuPont) in U.S. Pat. No. 4,311,863 (Jan. 19, 1982) discloses the use of a potassium, cesium or rubidium fluoride catalyst in aqueous solution.

The product has also been prepared from dichlorotetrafluoroethanes by hydrogenolysis, as in the process described by ICI in British Pat. No. 1,578,933 (Nov. 12, 1980), where a catalyst consisting of palladium on either an inactivated carbon or an alumina support is used in the presence of hydrogen.

Chromium catalysts are well known for fluorination reactions in general. Scherer et al. (Hoechst) in U.S. Pat. Nos. 3,660,307 (May 2, 1972) and 3,859,424 (Jan. 7, 1975) disclose catalysts prepared by reacting a hydrated oxide of trivalent chromium with hydrogen fluoride to form a trivalent chromoxy fluoride. The catalyst disclosed in Knaak (DuPont), U.S. Pat. No. 3,978,145 (Aug. 31, 1976) is a hexagonal-CrOOH (again including trivalent chromium), while that disclosed in Knaak (DuPont), U.S. Pat. No. 3,992,325 (Nov. 16, 1976) is a gamma-CrOOH plus a metal fluoride. A black chromium oxide with empirical formula $Cr_2O_{3-6}$ obtained by calcining the hydrated oxide in the presence of oxygen is disclosed in Chapman et al. (ICI), U.S. Pat. No. 3,426,009 (Feb. 4, 1969) and Firth et al. (ICI), U.S. Pat. No. 3,755,477 (Aug. 28, 1973). This catalyst was only able to form 1,1,1-trifluoro-2-chloroethane, however.

Chromium in combination with alumina has also been disclosed. One example is Japanese Patent No. 40,695 (Central Glass, Sept. 22, 1981) where trivalent chromium on alumina was used for the fluorination of $CCl_2F-CClF_2$ to $CClF_2-CClF_2$. Ruh et al. (Dow), U.S. Pat. No. 2,744,148 (May 1, 1956) disclose a catalyst consisting of aluminum fluoride, alumina and a metal halide in which the metal may be cobalt, chromium or others. Japanese Patent No. 24,925 (Central Glass, July 24, 1978) discloses a catalyst prepared by impregnating gamma-alumina with $TiCl_3$ which is then fluorinated. Milks (Dow), U.S. Pat. No. 2,744,147 (May 1, 1956) discloses a catalyst consisting of cobalt, nickel or chromium fluoride on an alumina support.

SUMMARY OF THE INVENTION

It has now been discovered that a catalyst prepared by codepositing a hexavalent chromium oxide and a transition metal compound on alumina, followed by treating the alumina and codeposited compounds with hydrogen fluoride, is relatively effective in catalyzing the vapor phase reaction of a haloethane of the formula $CX_2=CHX$. The transition metal compound in this invention is one of the group consisting of titanium, zirconium, vanadium, molybdenum and manganese, and the X's in the haloethylene formula are chlorine or bromine or a combination thereof. The unusual discovery made in the course of this invention is that the combination of these codeposited species provides a relatively high rate of conversion and selectivity toward the desired 1,1,1,2-tetrafluoroethane, significantly greater than what one would except from the activity of either of the species taken alone.

DETAILED DESCRIPTION OF THE INVENTION AND PREFERRED EMBODIMENTS

The hexavalent chromium oxide used in the preparation of the catalyst of the present invention is preferably chromium trioxide ($CrO_3$), and may be deposited on the alumina in any form, crystalline or amorphous, hydrated or otherwise. The transition metal compound may vary similarly in form. The transition metal itself is one selected from the group consisting of titanium, zirconium, vanadium, molybdenum and manganese. Within this group, titanium, zirconium and vanadium are preferred. Titanium and zirconium are particularly preferred, and titanium is the most preferred. Any compound of the transition metal which is susceptible to fluorination may be used. Preferred such compounds are halides of the transition metals, particularly chlorides. The most preferred is titanium trichloride.

The alumina may also assume a variety of forms, amorphous or crystalline, gel or solid—in general, any form which is or can be converted to solid alumina.

Alumina particles or pellets are preferred, particularly gamma-alumina, with a surface area prior to codeposition of at least about 50 m$^2$/g. Surface areas of at least about 100 m$^2$/g are particularly preferred.

Codeposition of the chromium oxide and transition metal compound on the alumina may be done either simultaneously or sequentially. The method of codeposition will vary depending on the form of the alumina. Preferably, solid alumina is used, and codeposition is achieved by the use of aqueous solutions of the chromium oxide and transition metal compound. Codeposition in this manner is achieved according to techniques well known among those skilled in the art of solid phase catalyst preparation, and generally involve combining the aqueous solution with a porous alumina base and permitting full absorption of the solution by the base, followed by drying the wet particles in air. Elevated temperatures may be used to enhance the drying, provided that they do not cause sintering of the particles.

The relative amounts of the catalyst components may vary. For best results, the atomic ratio of chromium to transition metal will fall in the range of about 1:1 to about 10:1, preferably from about 1:1 to about 3:1, and the combined impregnants (chromic oxide and transition metal compound) will together comprise from about 1% to about 30% (weight basis), preferably about 5% to about 20%, of the finished catalyst.

Following the deposition, the catalyst components are fluorinated to produce the finished catalyst. This is preferably achieved by contacting the components with gaseous hydrogen fluoride, preferably in the absence of oxygen. It is accordingly appropriate to flush the system of any oxygen that may have been present during the drying step. The fluorination conditions may vary widely. In general, however, contact with hydrogen fluoride gas for at least about one hour at elevated temperature, preferably for about 2 to about 50 hours, and most preferably for about 3 to about 20 hours, will provide the best results. Preferred contact temperatures are at least about 100° C., with about 300° C. to about 500° C. particularly preferred. Atmospheric pressure will generally be satisfactory.

Treatment with hydrogen fluoride in the catalyst preparation is carried out so as to fluorinate a substantial portion of the catalyst components. All three of the components will be fluorinated to some extent. The fluorination of a substantial portion of these components will be indicated by the observance of an exotherm during the contact with the fluorinating agent, and may also be confirmed by analysis of the finished catalyst. While the degree of fluorination may vary, in most cases the finished catalyst will contain a fluorine-to-total metals ratio of at least about 0.5:1 (weight basis), preferably from about 1:1 to about 4:1.

The catalyst having now been formed, it is used in the fluorination of a trihaloethylene (where the halogens are chlorine, bromine, or a combination of chlorine and bromine) to 1,1,1,2-tetrafluoroethane. The reaction is conducted in the vapor phase, using vapor phase reactants over a solid catalyst. The preferred starting material is trichloroethylene. The ratio of hydrogen fluoride to trichloroethylene in the reactant mixture will generally be at least the stoichiometric ratio of the reaction. In general, the ratio on a mole basis will fall within the range of about 4:1 to about 20:1, preferably from about 5:1 to about 10:1. The reaction temperature may vary, although it must be high enough to keep all reactants in the vapor phase. For best results, a temperature in excess of about 200° C. will be used. Temperatures above about 300° C. are preferred, with about 350° C. to about 550° C. particularly preferred, and about 400° to about 500° C. the most preferred.

The residence time (i.e., the time in which the reactants remain in contact with the catalyst) may also vary. Residence times in excess of about 10 seconds will generally provide the best results, with about 30 to about 300 seconds preferred, and about 30 to about 100 seconds the most preferred. The pressure under which the reaction is performed may also vary, with about 0.5 to about 10 atmospheres preferred, and about 1 to about 3 atmospheres particularly preferred.

The reaction may be conducted in any conventional manner known among those skilled in the art for a vapor phase reaction catalyzed by a solid catalyst. Examples include passing the reaction mixture over a catalyst bed or through a packed column of catalyst particles, such as a tube of inert construction, optionally jacketed by a temperature control system.

The product mixture emerging from the reaction may be processed and treated in a variety of ways to achieve either concentration or purification of the desired 1,1,1,2-tetrafluoroethane or both. In many cases, the major impurity in the product mixture will be 1,1,1-trifluoro-2-chloroethane (FC 113a), which can be converted to the desired product either by further fluorination over the same catalyst system, or by using one of the catalysts known for this conversion. The Bell, Potter, Daikin and Gumprecht references noted above are disclosures in this regard. For product purification, conventional operations such as scrubbing and fractional distillation may be used.

The following examples are offered for purposes of illutration, and are not intended to limit the invention in any manner.

EXAMPLES

Catalysts for use in these examples were prepared by impregnating porous activity alumina particles with aqueous solutions of the catalytic agents, then drying the wet particles first in air at 105° C. for 16 hours and then under a helium flow at 350° C. until water release ceased. This was followed by treatment with hydrogen fluoride gas at 350° C. for about six hours, during which time a 60°–100° C. exotherm was observed. The alumina particles were either A-201 alumina (a product of Kaiser Aluminum and Chemical Corporation, Oakland, Calif.) in the form of −8, +60 mesh particles of a mixed transition alumina having a total pore volume of 0.53 cm$^3$/g and a surface area of 325 m$^2$/g or "sa" alumina (a product of Kaiser Aluminum and Chemical Corporation, Oakland, Calif.) in the form of −8 +60 mesh particles of pseudoboehmite gel (produced from dried extrudate) having a total pore volume of 0.8 cm$^3$/g and a surface area of 180 m$^2$/g. The catalytic agents were reagent grade CrO$_3$, TiCl$_3$, CrCl$_3$, CoCl$_2$, and NiCl$_2$. Also included among the catalysts were Cr$_2$O(OH)$_4$ on coke (2:1, v/v) as suggested by the prior art (U.S. Pat. Nos. 3,859,424 and 3,660,307).

To carry out the reactions, liquid trichloroethylene at 0.293 g/min was fed with a positive displacement pump into a preheater, and hydrogen fluoride was supplied at a metered rate from a cylinder to a preheater, the two streams combined at the selected reaction temperature to form a vaporized homogeneous feed mixture with a hydrogen fluoride to trichloroethylene ratio of 6:1 (mole basis). The feed mixture was then passed through a vertical nickel reactor tube 1.0 inch (2.54 cm) in internal diameter and 28 inches (71 cm) in height, filled with the catalyst particles and enclosed in insulated resistance heaters. The pressure in the reactor ranged generally from 2 to 8 psig (1.14–1.54 atmospheres), and the residence time was approximately 47 seconds.

The exit gas from the reactor was bubbled through 13% NaOH heated to 80° C. (to prevent condensation of trichloroethylene), then passed through a cold-water trap to separate excess trichloroethylene, and finally through a splitter to the sampling loop of a gas chromatograph. The latter was equipped with a 12-foot (3.6-meter) Carbowax 20M column and a thermal conductivity detector. Product identity was established by comparing the elution times with standards, and confirming the structures with GC-mass spectrometry.

The results are listed in the table below, where the following notations are used:

TCE: trichloroethylene FC 133a: $CF_3CH_2Cl$
FC 134a: $CF_3CH_2F$

Catalysts within the scope of the present invention are shown in Runs 1 throught 7, while others are shown for comparative effect in Runs 8 through 15. The "other" products referred to in the last column included $CCl=CHCl$ (FC 1121), $CCl_2=CHF$ (FC 1121a), $CF_3-CHClF$ (FC 124), $CHF_2-CClF_2$ (FC 124a), and $CF_3-CH_3$ (FC 143a). A partial analysis of the spent catalyst from Run No. 4 for chromium, aluminum and fluorine yielded 2.0% Cr, 28.2% Al and 62.3% F (weight basis).

It should first be noted that prior to their use in the trichloroethylene fluorination reactions, the catalyst particles had the following appearance: the A-201 impregnated with $CrO_3$ only was deep yellow; the A-201 impregnated with $CrO_3$ and $TiCl_3$ was light brown; and the A-201 impregnated with $TiCl_3$ only was white. This suggested that the chromium was in the Cr (VI) state whereas the titanium had oxidized to the Ti (IV) state. After use, all chromium catalysts consisted largely of green particles, with noticeable quantities of brown and black particles included. This indicated a likelihood that reduction of the chromium to Cr (III) had occurred during the reaction.

Comparing Runs 1 through 7 with Runs 9 through 12 indicates that the chromium/titanium combination is more effective than either of the components taken individually at the same level as the total—i.e., a synergistic effect. Run 8 indicates that the alumina support when used alone is entirely inactive.

A particularly promising result shown in the table is the high content of FC 133a in the impurities present in the product mixtures. This species is the last intermediate before FC 134a and is available for further reaction either by extending the catalyst contact time, raising the temperture, or recycling.

As for the hydrated chromium oxide in Runs 13 and 14, both the conversion and selectivity were generally inferior to those of Runs 1 through 7.

The foregoing is offered primarily for purposes of illustration. It will be readily apparent to those skilled in the art that further variations and substitutions in the procedural steps, conditions, and components described herein can be made without departing from the spirit and scope of the invention.

What is claimed is:

| Run No. | Catalyst | Reaction Temperature (°C.) | Conversion of TCE to Products (%) | Product Analysis (%) | | |
|---|---|---|---|---|---|---|
| | | | | FC 134a | FC 133a | Other |
| 1 | 6% $CrO_3$/3% $TiCl_3$ on A-201 | 500 | 68 | 20 | 50 | 30 |
| 2 | 6% $CrO_3$/3% $TiCl_3$ on A-201 | 500 | 61 | 11 | 63 | 26 |
| 3 | 6% $CrO_3$/3% $TiCl_3$ on sa | 500 | 90 | 4 | 37 | 59 |
| 4 | 6% $CrO_3$/3% $TiCl_3$ on sa | 400 | 98 | 12 | 81 | 7 |
| 5 | 6% $CrO_3$/3% $TiCl_3$ on sa | 350 | 92–87 | 5–11 | 91–76 | 4–13 |
| 6 | 4% $CrO_3$/2% $TiCl_3$ on sa | 500 | 86 | 17 | 63 | 20 |
| 7 | 6% $CrO_3$/3% $TiCl_3$ on A-201; $NH_4OH$ to pH 5 | 400 | 88 | 4 | 89 | 7 |
| | | 500 | 86 | 8 | 53 | 39 |
| Comparison Tests: | | | | | | |
| 8 | A-201 | 400 | 0 | — | — | — |
| | | 600 | 0 | — | — | — |
| 9 | 9% $CrO_3$ on A-201 | 450 | ~10 | ~0 | ~10 | — |
| 10 | 9% $CrO_3$ on A-201 | 450 | ~0 | — | — | — |
| 11 | 9% $CrO_3$ on A-201 | 500 | 47 | ~0 | ~75 | 25 |
| 12 | 9% $TiCl_3$ on A-201 | 500 | 50 | 0 | 0 | 100 |
| 13 | $Cr_2O(OH_4)$/coke, 1:2 v/v | 400 | 75 | 6 | 86 | 8 |
| 14 | $Cr_2O(OH_4)$/coke, 1:2 v/v | 400 | ~76 | 4 | 74 | 22 |
| | | 500 | ~90 | 6 | 43 | 51 |
| 15 | 2.5% $CoCl_2$/ 2.5% $CrCl_3$/ 2.5% $NiCl_2$ on A-201 | 450 | 64 | ~0 | 79 | 21 |

1. A process for preparing a fluorination catalyst, comprising:
   (a) codepositing from an aqueous solution hexavalent chromium oxide and a compound of a transition metal said transition metal selected from the group consisting of titanium, zirconium, vanadium, molybdenum and manganese at a chromium to transition metal atomic ratio of about 1:1 to about 10:1 on solid porous alumina particles having a surface area of at least about 50 m$^2$/g prior to said codeposited to produce impregnated alumina particles of which said hexavalent chromium oxide and said transition metal together comprise from about 5 to about 30 weight percent; and
   (b) contacting the product of step (a) with hydrogen fluoride gas from about 3 to about 20 hours at a temperature of about 300° C. to about 500° C.

2. A process in accordance with claim 1 in which said solid alumina particles have a surface area of at least about 100 m$^2$/g prior to said codeposition.

3. A process in accordance with claim 1 in which said transition metal is selected from the group consisting of titanium, zirconium and vanadium.

4. A process in accordance with claim 1 in which said transition metal is selected from the group consisting of titanium and zirconium.

5. A process in accordance with claim 1 in which said transition metal is titanium.

6. A process in accordance with claim 1 in which said transition metal is trivalent titanium.

7. A process in accordance with claim 1 in which said compound of a transition metal of step (a) is a titanium trihalide.

8. A process in accordance with claim 1 in which said compound of a transition metal of step (a) is titanium trichloride.

9. A process in accordance with claim 1 in which the atomic ratio of chromium to transition metal in step (a) is from about 1:1 to about 3:1.

10. A process in accordance with claim 1 in which said hexavalent chromium oxide and said transition metal compound together comprise from about 5 to about 20 weight percent of said catalyst.

11. A fluorination catalyst prepared by
   (a) codeposition from an aqueous solution hexavalent chromium oxide and titanium trichloride at a chromium:titanium atomic ratio of about 1:1 to about 3:1 on solid porous alumina particles having a surface area of at least about 100 m$^2$/g to produce impregnated alumina particles of which said hexavalent chromium oxide and said titanium trichloride together comprise from about 5 to about 20 weight percent; and
   (b) contacting the product of step (a) with hydrogen fluoride gas for about 3 to about 20 hours at a temperature of about 300° C. to about 500° C.

* * * * *